US008216518B2

(12) United States Patent
Chau et al.

(10) Patent No.: US 8,216,518 B2
(45) Date of Patent: Jul. 10, 2012

(54) PLASMON RESONANCE SENSING APPARATUS AND SENSING SYSTEM THEREOF

(75) Inventors: Lai-Kwan Chau, Chiayi (TW); Wei-Zhe Chang, Chiayi County (TW); Shin-Huei Chen, Tainan County (TW)

(73) Assignee: National Chung Cheng University, Chia-Yi (TW)

( * ) Notice: Subject to any disclaimer, the term of this patent is extended or adjusted under 35 U.S.C. 154(b) by 130 days.

(21) Appl. No.: 12/454,209

(22) Filed: May 13, 2009

(65) Prior Publication Data

US 2010/0123900 A1 May 20, 2010

(30) Foreign Application Priority Data

Nov. 20, 2008 (TW) ................................ 97144992 A

(51) Int. Cl.
G01N 21/55 (2006.01)
(52) U.S. Cl. .................. 422/82.11; 356/445; 422/82.05; 435/287.2
(58) Field of Classification Search .... 422/82.01–82.12, 422/81.01; 356/38, 445; 977/810; 385/12, 385/129, 13, 25; 435/287.2
See application file for complete search history.

(56) References Cited

U.S. PATENT DOCUMENTS

| | | | | |
|---|---|---|---|---|
| 5,325,458 A * | 6/1994 | Morrow et al. | ............... | 385/125 |
| 6,480,282 B1 * | 11/2002 | Chinowsky et al. | .......... | 356/445 |
| 7,058,272 B2 * | 6/2006 | Bourdelais et al. | ........... | 385/129 |
| 7,599,066 B2 * | 10/2009 | Fukuda | ........................ | 356/445 |
| 2004/0150818 A1 * | 8/2004 | Armstrong et al. | .......... | 356/301 |
| 2006/0034729 A1 * | 2/2006 | Poponin | ...................... | 422/82.05 |
| 2006/0268408 A1 * | 11/2006 | Toussaint et al. | ............. | 359/487 |

OTHER PUBLICATIONS

Chang, et al., Localized Plasmon Resonance Sensors: Comparison of Several Waveguide-Based Configurations, Published Jul. 2008, Seminar held on Mar. 24-25, 2008.

* cited by examiner

*Primary Examiner* — In Suk Bullock
*Assistant Examiner* — Sharon Pregler
(74) *Attorney, Agent, or Firm* — Hudak, Shunk & Farine Co. LPA

(57) ABSTRACT

A plasmon resonance sensing system includes a light source, a waveguide component and a photon detector. The light source provides an incident light. The waveguide component has a tubular internal wall and a noble metal nanoparticle layer disposed on the tubular internal wall and contacted with a desired testing matter. The waveguide component is made of a light transmitting material for guiding the incident light to have an interaction with the noble metal nanoparticle layer. The photon detector detects an emergent light exiting the waveguide component after the interaction of the noble metal nanoparticle layer with the desired testing matter. The system further includes a first optical fiber installed between the light source and the waveguide component for transmitting the incident light to the waveguide component, a lens and a second optical fiber. The lens collects and transmits the emergent light to the photon detector through the second optical fiber.

20 Claims, 15 Drawing Sheets

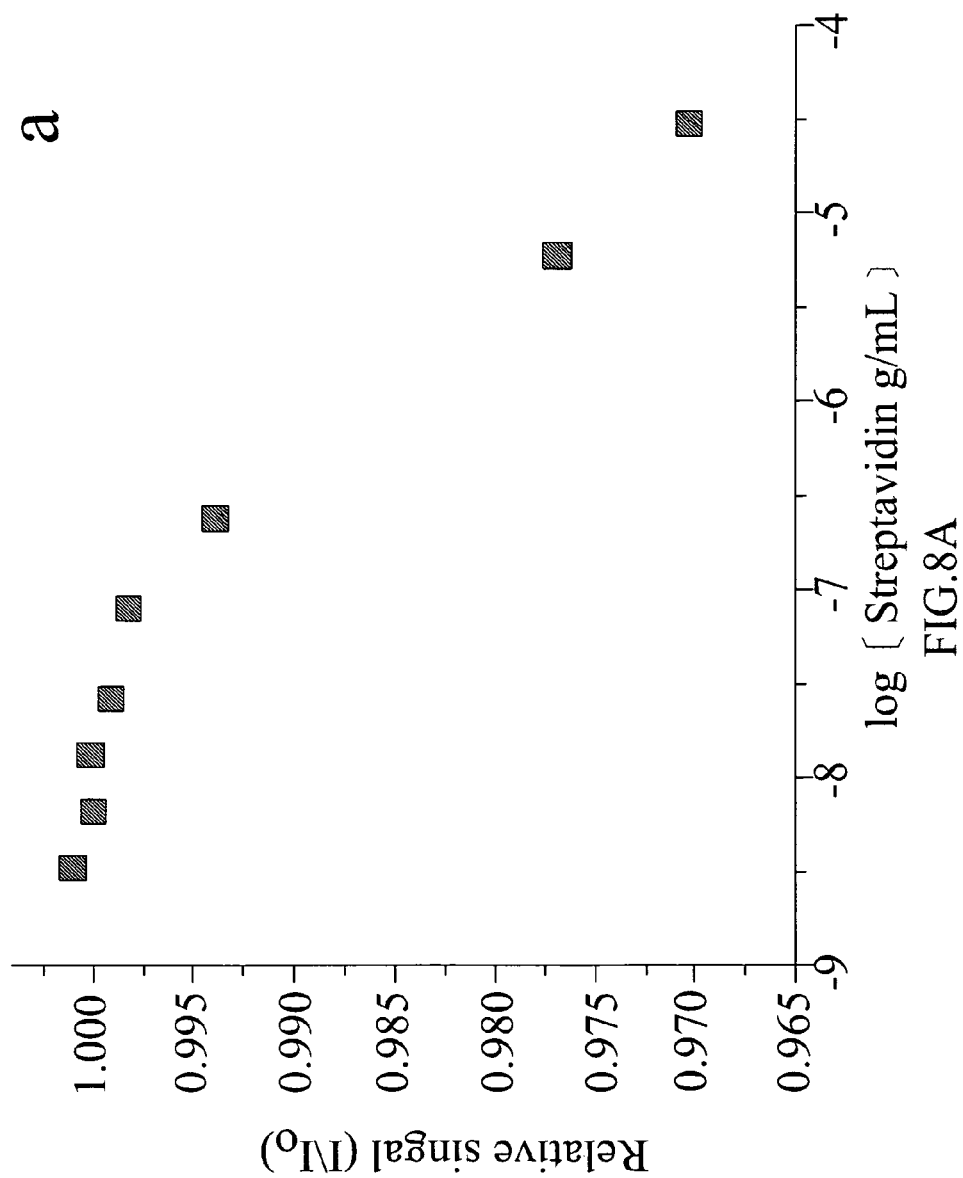

PLASMON RESONANCE SENSING APPARATUS AND SENSING SYSTEM THEREOF

FIELD OF THE INVENTION

The present invention generally relates to a plasmon resonance sensing apparatus and a sensing system thereof, and more particularly to a surface plasmon resonance sensing system using a tubular waveguide component as a container of a desired testing sample.

BACKGROUND OF THE INVENTION

In general, surface plasmon resonance refers to a phenomenon having a light at a certain incident angle (the resonance angle) hits a thin metal film so that the light reflected from the film drops to a minimum intensity. However, light in the sample medium cannot naturally excite surface plasmon resonance and a high refractive index-prism or grating is required. When a light beam is incident through the prism on the surface of the thin metal film at total reflection angle, the evanescent wave interacts with the sample, and at the resonance angle, it couples with the surface plasmon. Hence, a fraction of the incident light energy transfers to surface plasmon resonance and the energy of the reflected light diminishes. The resonance angle is extremely sensitive to the dielectric permittivity at the interface. Thus, surface plasmon resonance can be used for biospecific interaction analysis.

A surface plasmon resonance sensing system is sensing system made in accordance with the aforementioned surface plasmon resonance phenomenon. Since a surface plasmon resonance sensor is sensitive to the local refractive index change at the metal/sample interface, it is not necessary to label an analyte molecule with a spectroscopic or electrochemical signature, and thus the surface plasmon resonance sensors possess the advantages of label-free and real-time detection, short analysis time, and high sensitivity. It has been applied extensively for detecting biological molecules.

A free electron cloud on the metal nanoparticle surface is excited by an electromagnetic field with a specific frequency to produce a collective dipole resonance, but the oscillating electron cloud is restricted in the neighborhood of nanoparticles, and thus such a resonance is called a localized plasmon resonance (LPR). It is interesting to find that if the environmental refractive index around the metal nanoparticles is changed, the frequency and the extinction cross-section of the LPR band will be changed accordingly. If the environmental refractive index around the metal nanoparticles increases, the peak wavelength of the LPR band will shift to a long wavelength and the extinction cross-section of the LPR band will increase. While observing the characteristic of a scattered light, we may find that when the refractive index of the medium rises, the peak wavelength in the spectrum of the scattered light also shifts to a long wave and with an increase of the light intensity.

In recent years, the development of nano materials has become a main subject for researchers and manufacturers, and the industries such as optoelectronics, communications and medical instruments spend a lot of effort on the research and development of the nano materials. A primary reason of the nano materials becoming favorable materials resides on that the nano materials provide properties totally different from the characteristics of the original sample. In the prior art, noble metal nanoparticles are used to excite the localized plasmon resonance (LPR) to substitute the traditional way of using noble metal films to excite the surface plasmon resonance (SPR) so as to improve the sensitivity and other analytical performance features (e.g., ease of miniaturization, simplicity in construction, and cost) of the sensor. At present, the technology of synthesizing nanoparticles is well developed, and basically divided into chemical and physical methods. The physical methods include a metal vaporization method, a laser etching method and a sputtering method, etc, and the metal vaporization method is the most commonly used one among these methods. The chemical methods include a reduction method and an electrolysis method, etc, and the reduction method is the most commonly used and important one. However, technologies and science advance rapidly, the requirement for the sensitivity of the sensors becomes increasingly higher, and thus it is an important subject for related researchers and manufacturers to improve the sensitivity and analytical performance of the sensor.

SUMMARY OF THE INVENTION

Therefore, it is a primary objective of the present invention to overcome the shortcomings of the prior art by providing a plasmon resonance sensing apparatus and a sensing system thereof.

The light waveguide technology is used to produce a plurality of total internal reflections via the evanescent wave phenomenon at the reflection interface to accumulate the signal change of light attenuation by the LPR. As described in the prior art, if the noble metal nanoparticle senses a change of the environmental refractive index, the resonance frequency of the LPR band will be changed as well, and thus the spectrum of the absorbed light or the spectrum of the scattered light will be affected. In an optical waveguide modified with noble metal nanoparticles, the light of a specific frequency at the position of each reflection interface will interact with the nanoparticles to excite the LPR. The more the number of times of reflections, the more significant is the effect on the light intensity of this frequency. While observing the characteristic of light attenuation, we may find that after the incident light has gone through a plurality of total internal reflections, the light signal exiting the waveguide is attenuated. While observing the characteristic of a scattered light, we may find that the intensity of the scattered light is increased. In summary, a plurality of total internal reflections may amplify the quantity of signal change due to the LPR phenomenon to improve the sensitivity. Finally, a tubular waveguide localized plasmon resonance (LPR) sensing unit is used as a transducer as well as a container for accommodating a sample in a stand-alone manner or samples arranged in an array, and a light source and a photon detector are used together to achieve a sensing capability with a high performance output.

To achieve the foregoing objective, the present invention provides a plasmon resonance sensing apparatus comprising: a waveguide component, having a tubular internal wall and a noble metal nanoparticle layer disposed on a surface of the tubular internal wall for contacting with a desired testing sample, for guiding the incident light to have an action with the noble metal nanoparticle layer to quantitatively determine the analyte in the desired testing sample.

To achieve the foregoing objective, the present invention further provides a plasmon resonance sensing system comprising: at least one light source for providing at least one incident light; at least one waveguide component, having a tubular internal wall; a noble metal nanoparticle layer, disposed on the tubular internal wall for contacting a desired testing sample; at least one photon detector, used for detecting at least one emergent light exiting the tubular waveguide, where the waveguide component guides the incident light to have an action with the noble metal nanoparticle layer in order to quantitatively determine the analyte in the desired testing sample.

The present invention uses a multiple of a tubular waveguide with a plurality of total internal reflections to accumulate the signal change of light attenuation by the LPR to improve the performance of the signal-to-noise ratio. Since the tubular waveguide substrate is adopted, the sensing system has the advantages of a small size and a self-contained sample holding design. If the tubular waveguides are arranged in an array, the sensing system may have a high sensitivity as well as a high throughput.

With these and other objects, advantages, and features of the invention that may become hereinafter apparent, the nature of the invention may be more clearly understood by reference to the detailed description of the invention, the embodiments and to the several drawings herein.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

FIG. 8A is a graph of relative signal (I/Io) versus logarithm concentration of streptavidin obtained by using a plurality of point light sources in accordance with a third preferred embodiment of the present invention;

DETAILED DESCRIPTION OF THE INVENTION

To make it easier for our examiner to understand the technical characteristics of the present invention, preferred embodiments with accompanying drawings are used for the detailed description of the invention, wherein same elements are represented by same respective numerals.

Those of ordinary skilled in the art will realize that the following detailed description of the exemplary embodiment(s) is illustrative only and is not intended to be in any way limiting. Other embodiments will readily suggest themselves to such skilled persons having the benefit of this disclosure. Reference will now be made in detail to implementations of the exemplary embodiment(s) as illustrated in the accompanying drawings. The same reference indicators will be used throughout the drawings and the following detailed description to refer to the same or like parts.

Figure 1:
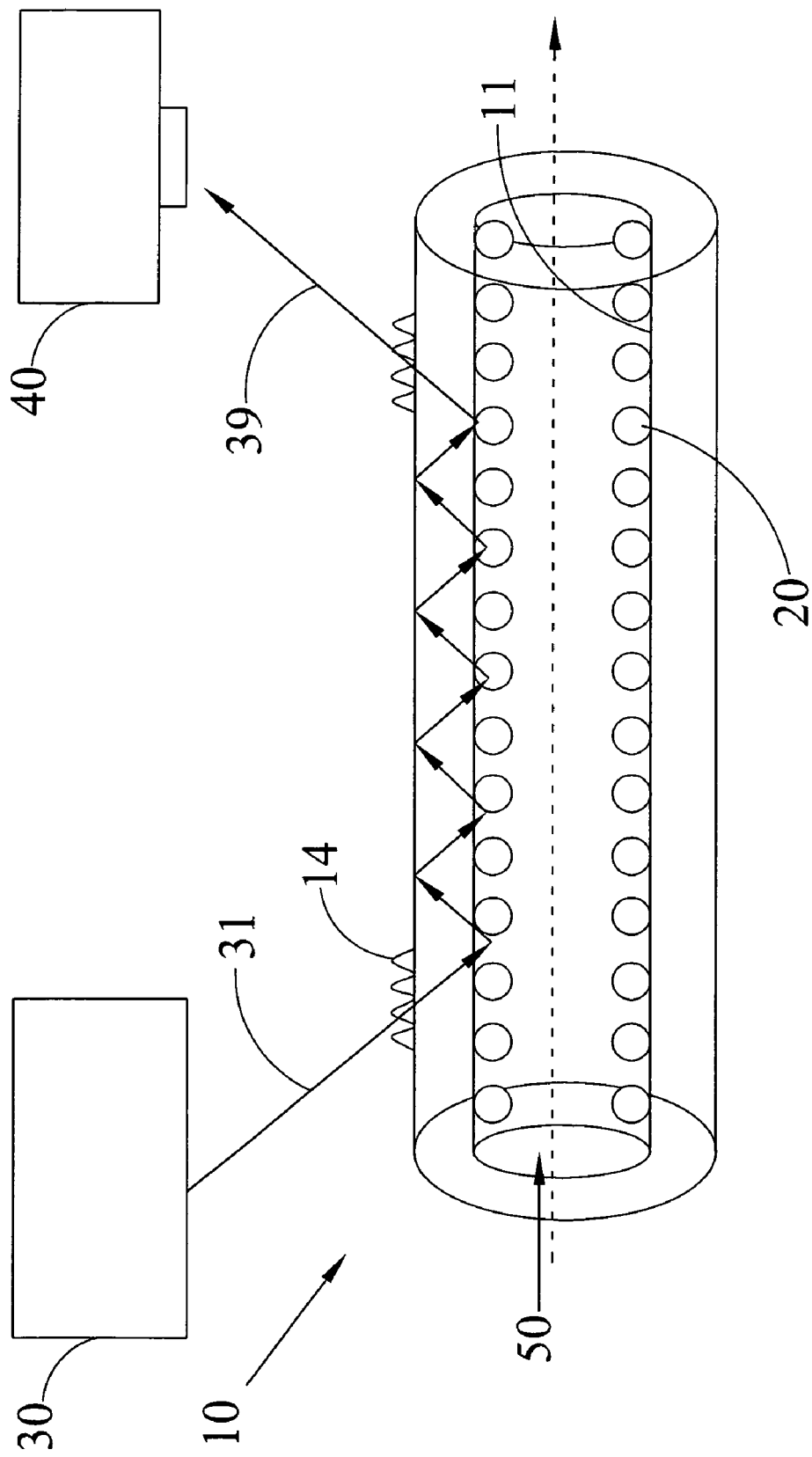
FIG. 1 is a schematic view of a tubular waveguide plasmon resonance sensing system in accordance with a first preferred embodiment of the present invention.

With reference to FIG. 1 for a schematic view of a tubular waveguide plasmon resonance sensing system in accordance with a first preferred embodiment of the present invention, the plasmon resonance sensing apparatus comprises a waveguide component 10 and a noble metal nanoparticle layer 20, and the waveguide component has a tubular internal wall 11, and the noble metal nanoparticle layer 20 is disposed on a surface of the tubular internal wall. The noble metal nanoparticle layer 20 is composed of a plurality of noble metal nanospheres, a plurality of noble metal nanorods or a plurality of noble metal nanoshells. This embodiment further comprises a light source 30 and a photon detector 40, and the light source 30 uses a single frequency light (such as LASER) or a narrowband light wave (such as LED) as an incident light 31, and a grating 14 guides the incident light to the waveguide component 10, and the waveguide component 10 is made of a light transmitting material for guiding the incident light 31 to have an action with the noble metal nanoparticle layer 20 and an emergent light 39 exiting from anther grating and is collected at the photon detector 40. If a desired testing sample 50 is passed through the waveguide component 10, the noble metal nanoparticle layer 20 contacts with the desired testing sample 50 and results in a change of light attenuation by the LPR effect, and finally give rise to a change of the signal of the emergent light 39.

Figure 2A:
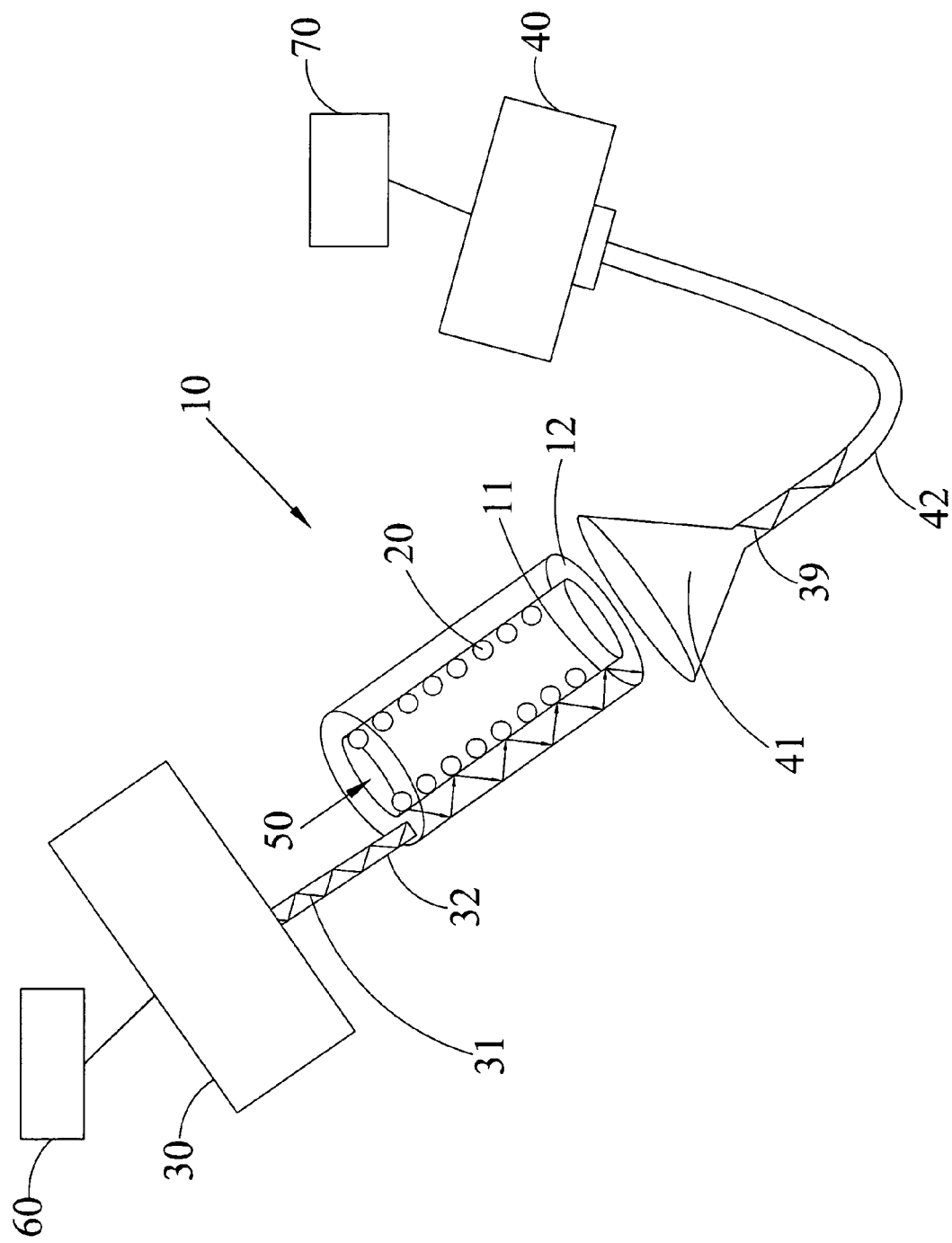
FIG. 2A is a schematic view of a tubular waveguide plasmon resonance sensing system in accordance with a second preferred embodiment of the present invention.
Figure 2B:
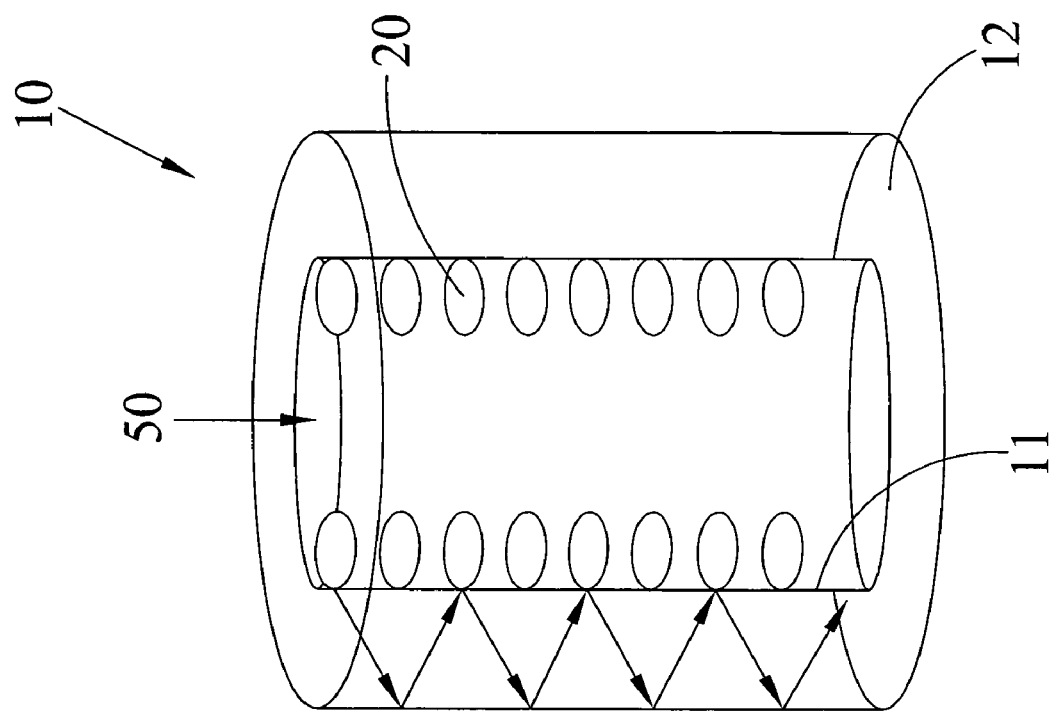
FIG. 2B is a schematic view of using a tubular waveguide device to carry out a desired testing of a sample in accordance with a second preferred embodiment of the present invention.

With reference to FIG. 2A for a schematic view of a tubular waveguide plasmon resonance sensing system in accordance with a second preferred embodiment of the present invention, the sensing system comprises at least one light source 30, for supplying at least one incident light 31; at least one waveguide component 10 for guiding the incident light 31 to have an action with the noble metal nanoparticle layer 20, which is disposed on a surface of the tubular internal wall 11 and is contacting with a desired testing sample 50; at least one photon detector 40, for detecting at least one emergent light 39 emitted after the interaction of the noble metal nanoparticle layer 20 with the desired testing sample 50. The preferred embodiment further comprises at least one first optical fiber 32 disposed between the light source 30 and the waveguide component 10 for transmitting the incident light 31 to the waveguide component 10; a lens 41 and a second optical fiber 42. The lens 41 collects the emergent light 39 and uses the second optical fiber 42 to transmit the emergent light 39 to the photon detector 40. In this embodiment, the light source 30 is a single frequency light, a narrowband light or a white light, and a planar sealed bottom 12 is disposed at an end of the waveguide component 10 (as shown in FIG. 2B), such that the waveguide component 10 by itself is a sample container and is also a sensing unit. This embodiment further comprises a function generator 60 for driving the light source 30 so that the incident light is modulated, and a lock-in amplifier 70 for reducing system noises.

Figure 3A:
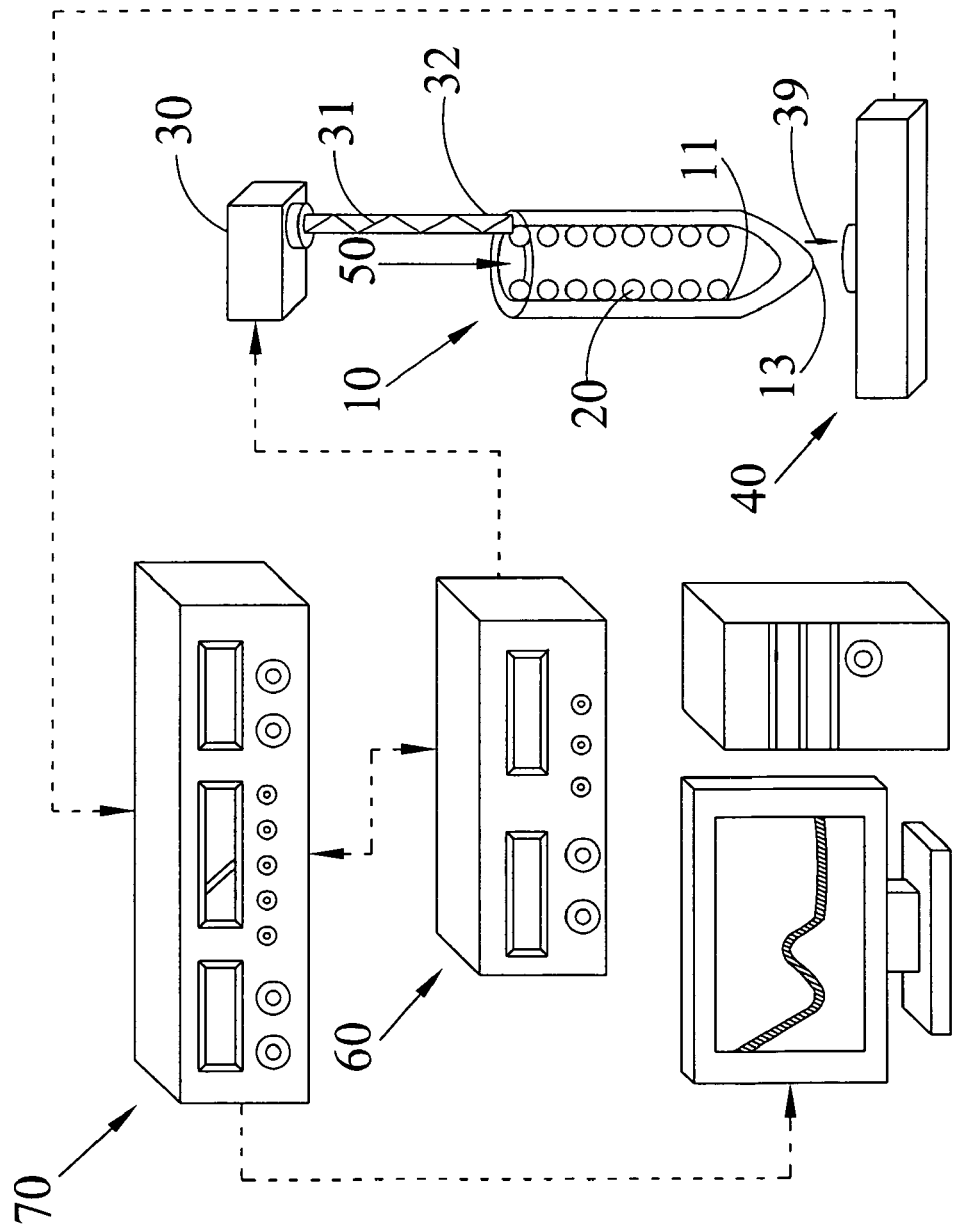
FIG. 3A is a schematic view of a tubular waveguide plasmon resonance sensing system in accordance with a third preferred embodiment of the present invention.
Figure 3B:
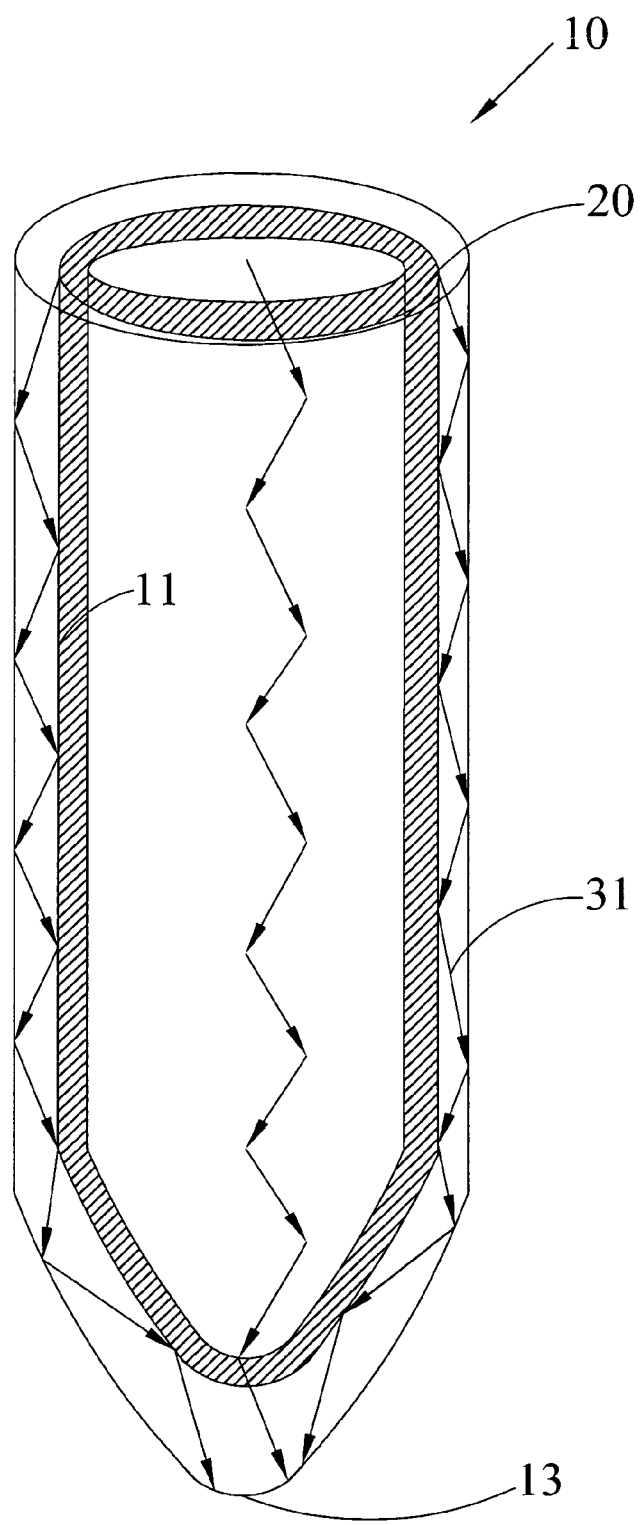
FIG. 3B is a schematic view of using a conical tubular waveguide device to carry out a desired testing of a sample in accordance with a third preferred embodiment of the present invention.

With reference to FIG. 3A for a schematic view of a tubular waveguide plasmon resonance sensing system in accordance with a third preferred embodiment of the present invention, the plasmon resonance sensing apparatus (as shown in FIG. 3B) comprises a waveguide component 10 and a noble metal nanoparticle layer 20, and the waveguide component 10 has a tubular internal wall 11 and a conical sealed end 13, and the noble metal nanoparticle layer 20 is disposed on the surface of the tubular internal wall 11 and the internal wall of the conical sealed end 13. In this embodiment, the plasmon resonance sensing system further comprises at least one light source 30 for supplying at least one incident light 31; a waveguide component 10, having a tubular internal wall 11 and a conical sealed end 13; a noble metal nanoparticle layer 20, disposed on the surface of the tubular internal wall 11 and the internal wall of the conical sealed end 13 for contacting a desired testing sample 50; at least one photon detector 40, for detecting at least one emergent light 39 emitted after having an action with the noble metal nanoparticle layer 20 in order to quantitatively determine the analyte in the desired testing sample 50, wherein the waveguide component 10 guides the incident light 31 to interact with the noble metal nanoparticle layer 20. This embodiment further comprises: at least one first optical fiber 32, for receiving the light from the light source 30 and transmitting the incident light 31 to the waveguide component 10; a function signal generator 60, for driving the light source 30 so that the incident light is modulated; and a lock-in amplifier 70, for reducing system noises.

Figure 4A:
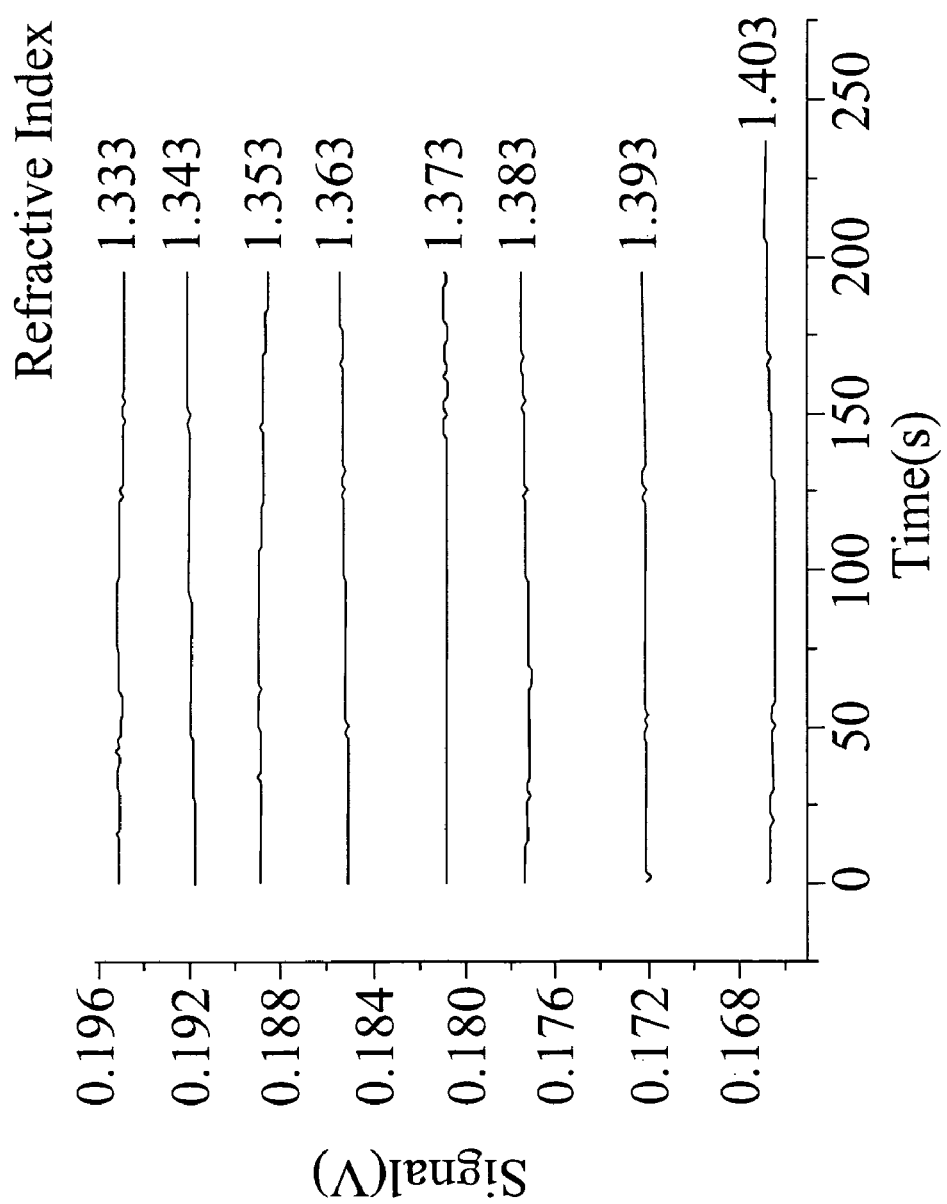
FIG. 4A is a graph of signal versus time for a third embodiment of using a conical tubular waveguide device to carry out a desired testing of samples with different refractive indexes in accordance with the present invention.
Figure 4B:
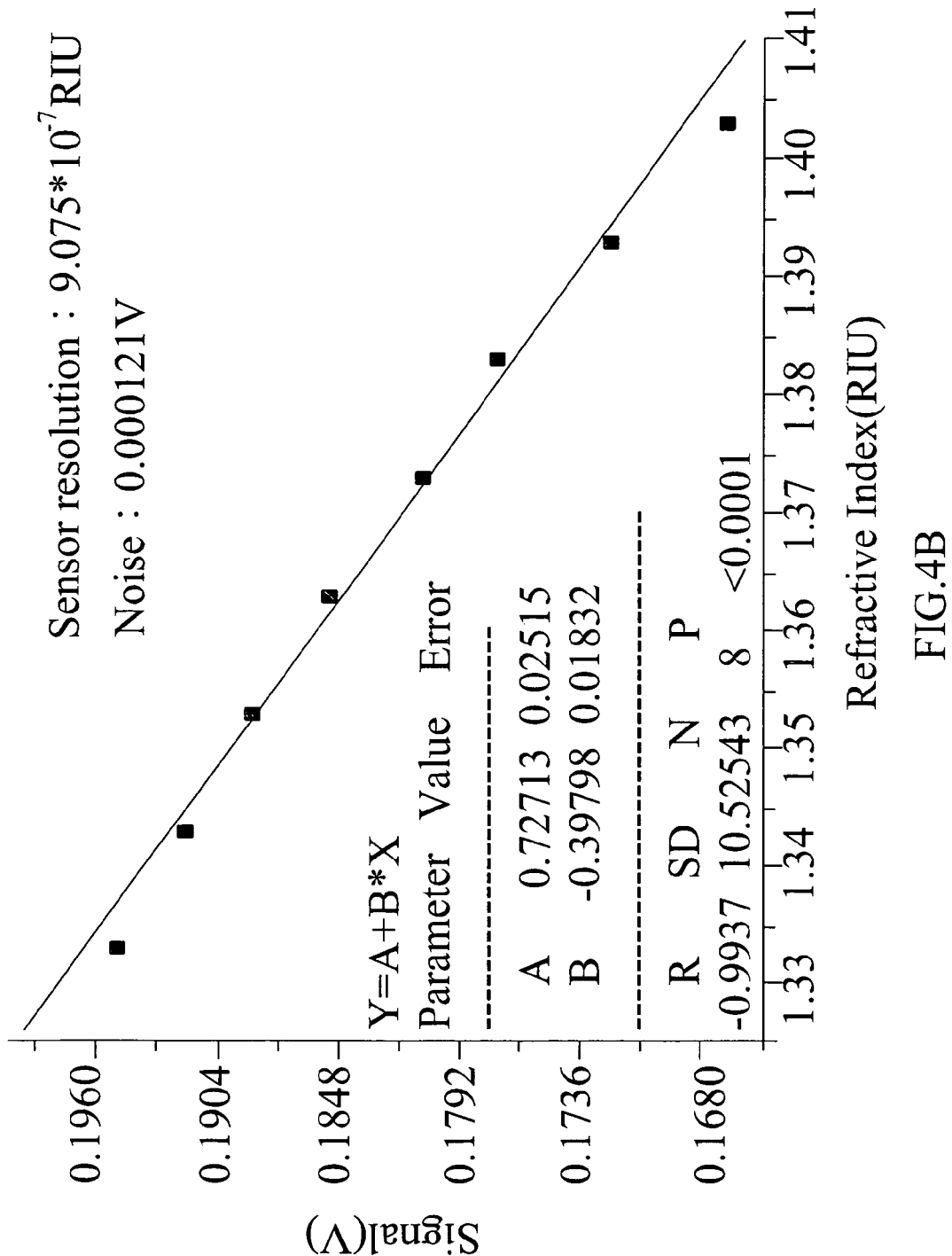
FIG. 4B is a graph of signal versus refractive index for a third embodiment of using a conical tubular waveguide device to carry out a desired testing of samples with different refractive indexes in accordance with the present invention.

In a system structure as shown in FIG. 3A, a waveguide substrate is made of glass, and the noble metal nanoparticles are gold nanospheres. A function generator is used for driving a light emitting diode (LED) that emits light with a wavelength of 530 nm by using a square wave of 1000 times per second, and finally a reading is read from a computer after a lock-in amplifier has processed and amplified the signal. In other words, if the light source is an LED, the experimental result from the sensing system shows a change of signal versus refractive index as shown in FIG. 4A. The emergent light signal from the light waveguide will vary with the refractive index of the sample solution, and the signal intensity measured by the sensor is obtained by using a steady-state signal as an output, and the system noise ($\sigma$) is $1.21 \times 10^{-4}$ V. In FIG. 4B, the graph of the output signal shown in FIG. 4A versus refractive index of the sample solution is given, and the emergent light intensity from the waveguide has a good linear relation with the solution refractive index, wherein the value of correlation coefficient (R) is equal to 0.9937, and the slope (m) of such linear relation is equal to 0.398V/RIU. Therefore, the sensor resolution is calculated as $9.08 \times 10^{-4}$ RIU (Note: We define the minimum detectable signal as a signal with a magnitude equals to three times of the noises, and the numeric value of the corresponding change of refractive index is the sensor resolution. The sensor resolution is calculated by the mathematic formula=$3\sigma/m$ or $3 \times 0.000121 \div 0.398$).

Figure 5A:
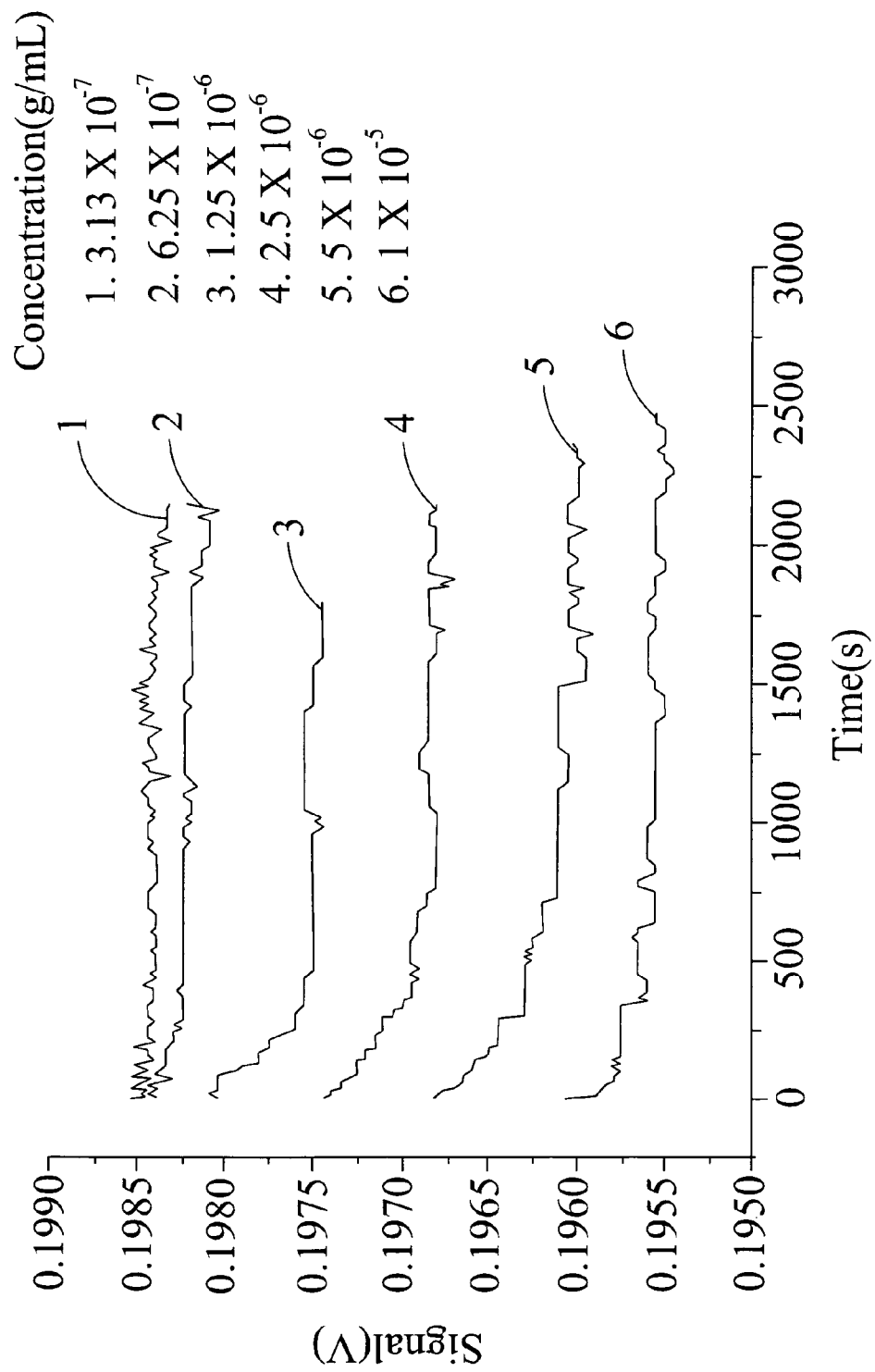
FIG. 5A is a graph of signal versus time for a tubular waveguide plasmon resonance sensing system using streptavidin solutions of different concentrations.
Figure 5B:
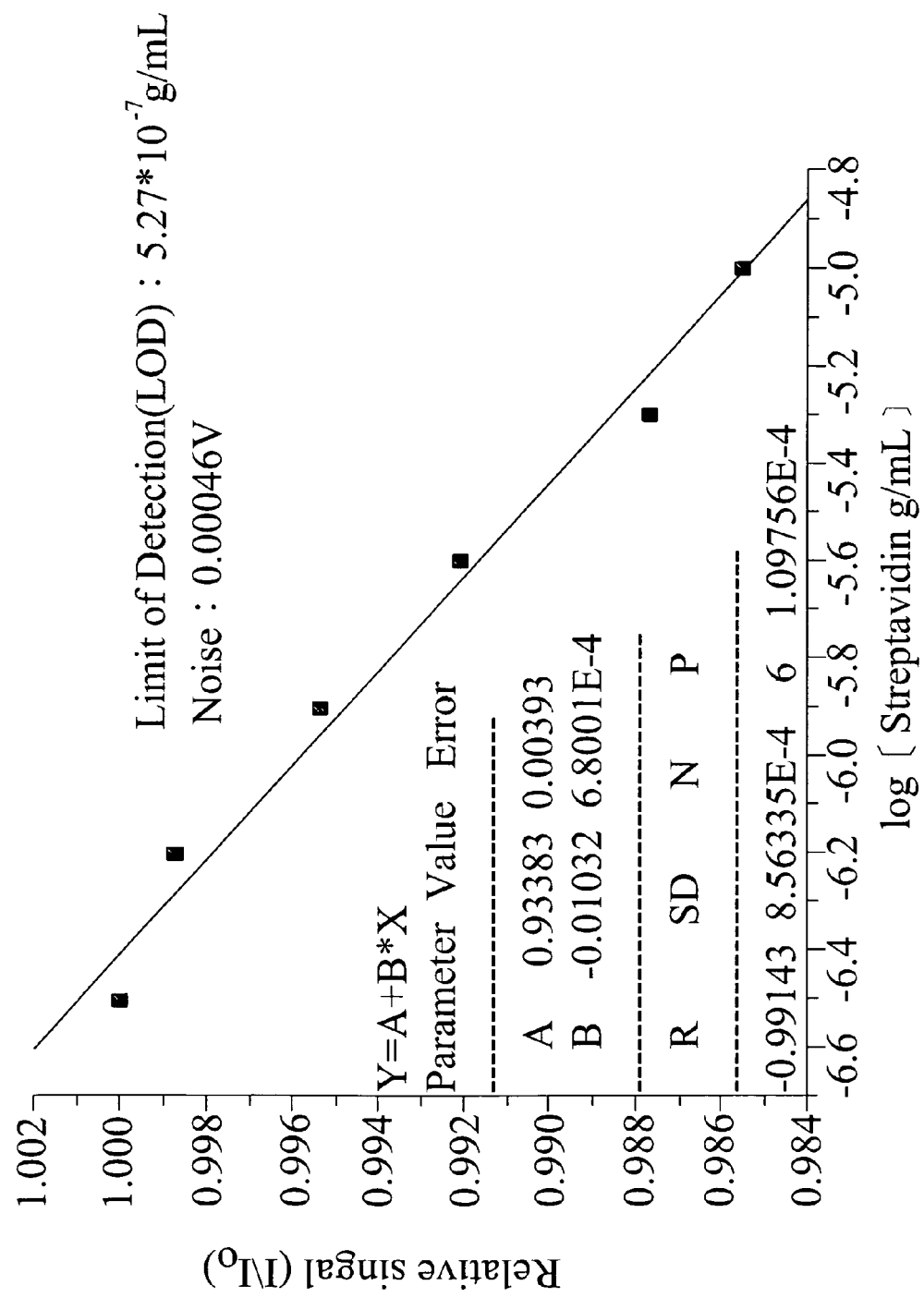
FIG. 5B is a graph of relative signal (I/Io) versus logarithm concentration of streptavidin obtained by a tubular waveguide plasmon resonance sensing system.

Biotin-functionalized gold nanoparticles on an internal wall of a glass tube may be used to detect streptavidin, and the related sensing system is shown in FIG. 3A. From FIG. 5A, we may find that after samples with different concentrations of streptavidin are injected into the glass tube, the emergent light signal from the waveguide will drop and then reach a steady state. The occurrence of such phenomenon is due to the binding of streptavidin with immobilized vitamin H (biotin) molecules, such that the dielectric constant around the gold nanoparticle surface will increase gradually and then reach an equilibrium state, and the extinction cross-section of the LPR band increases, and finally the emergent light signal emitted from the waveguide is attenuated. If a signal reaches a steady state, it means that the molecular recognition reaction has reached equilibrium. Finally, if the relation between a relative signal ($I/I_O$, wherein I is a sample signal, and $I_o$ is a blank signal) and a concentration logarithm (log [C]) of each steady-state signal is analyzed, we obtain a straight line as shown in FIG. 5B. Now, the system noise is equal to $4.6 \times 10^{-4}$ V, so that we calculate the detection limit of the sensing system with respect to streptavidin is equal to $5.27 \times 10^{-7}$ g/mL (or $8.78 \times 10^{-9}$M).

Figure 6:
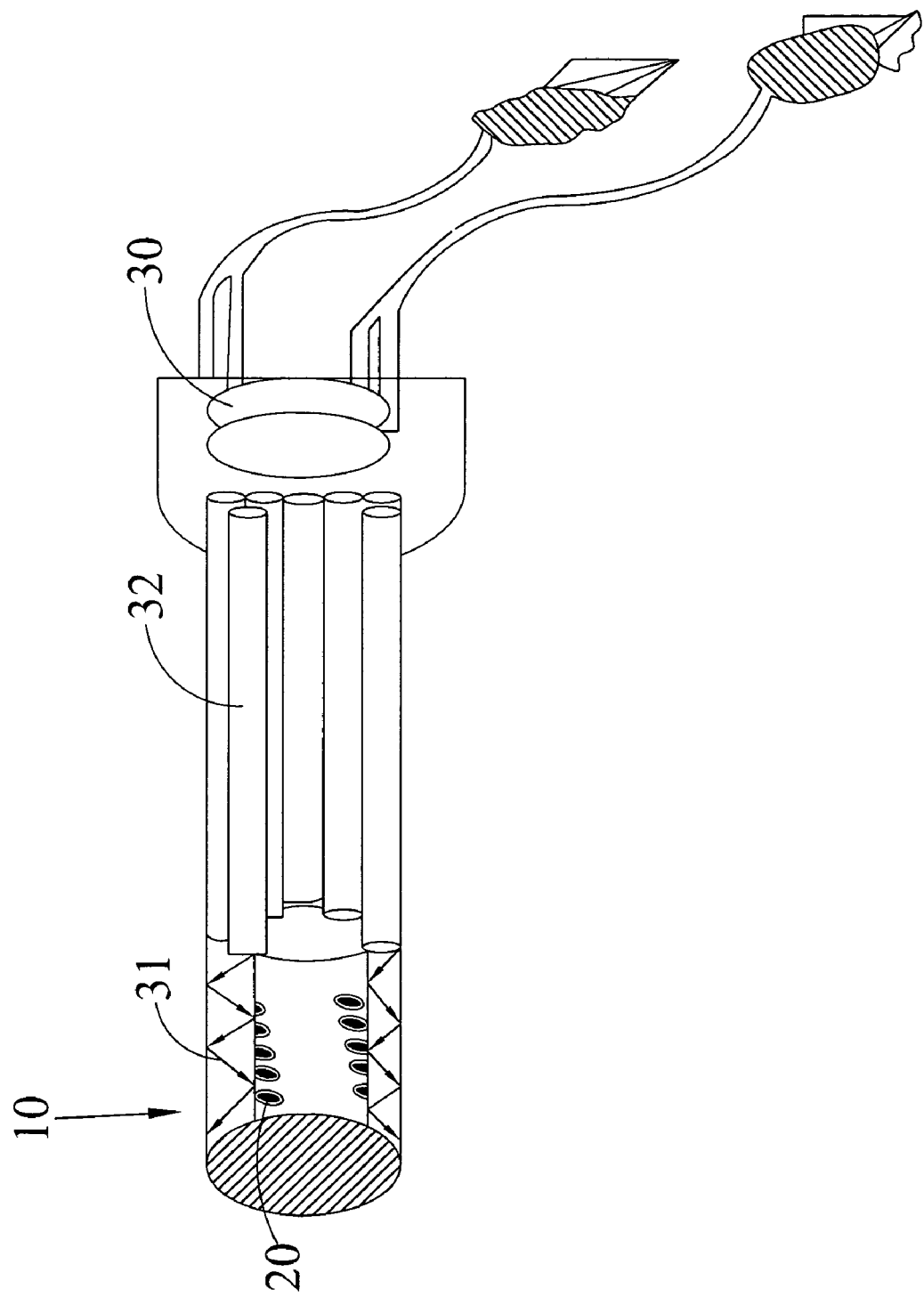
FIG. 6 is a schematic view of using a plurality of point light sources to provide an incident light in accordance with a second preferred embodiment of the present invention.

With reference to FIG. 6 for a schematic view of using a plurality of point light sources to provide an incident light in accordance with a second preferred embodiment of the present invention, the second preferred embodiment further comprises a plurality of light sources 30 or a plurality of first optical fibers 32 for coupling and emitting a plurality of incident lights 31 to different locations of the wall at the open end of the waveguide component 10 to improve the overall effect of the LPR phenomenon of the noble metal nanoparticle layer 20, so as to improve the sensitivity of the sensing system.

Figure 7A:
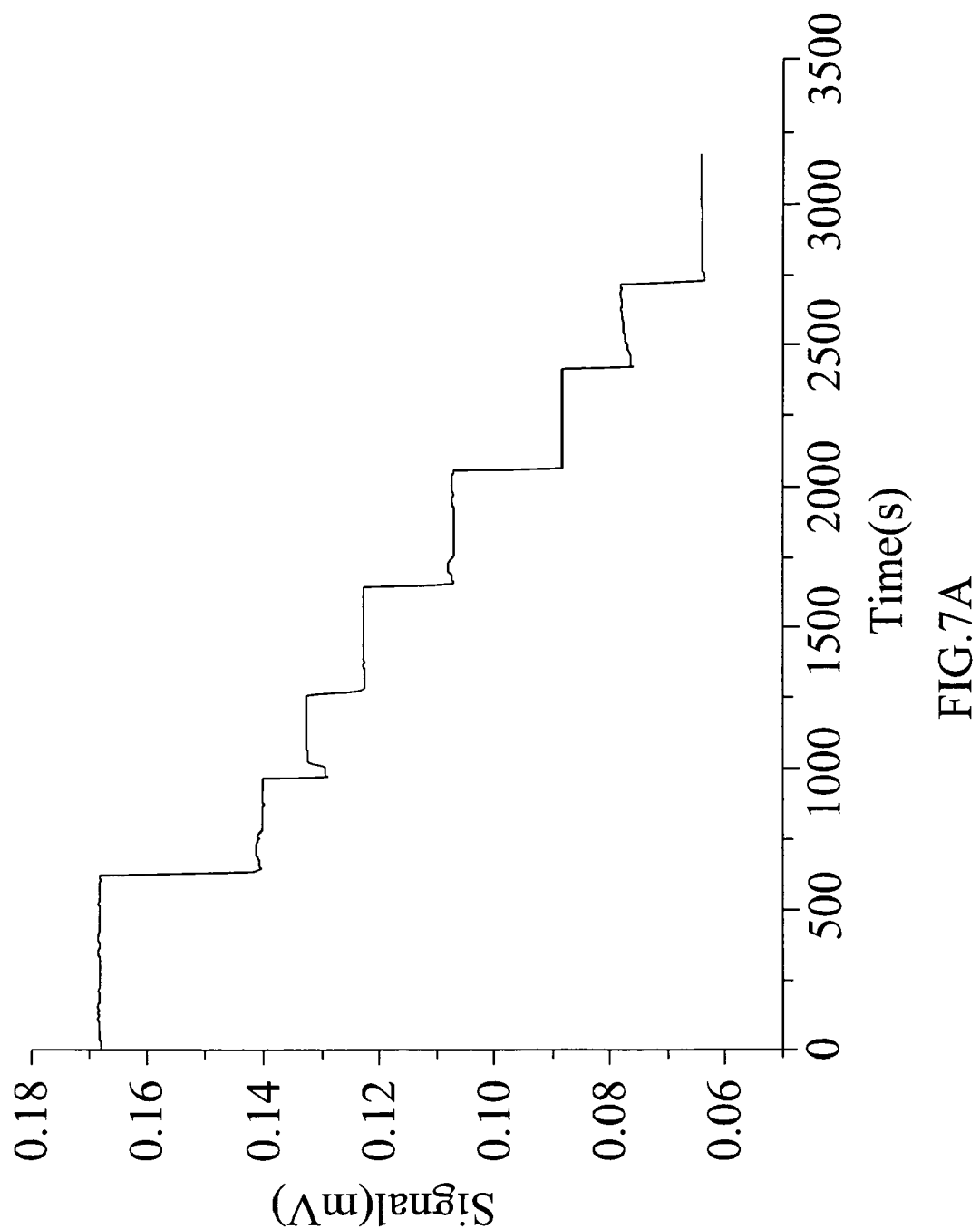
FIG. 7A is a graph of emergent light intensity versus time of a tubular waveguide plasmon sensing system with solutions of different refractive indexes in accordance with a second preferred embodiment of the present invention.
Figure 7B:
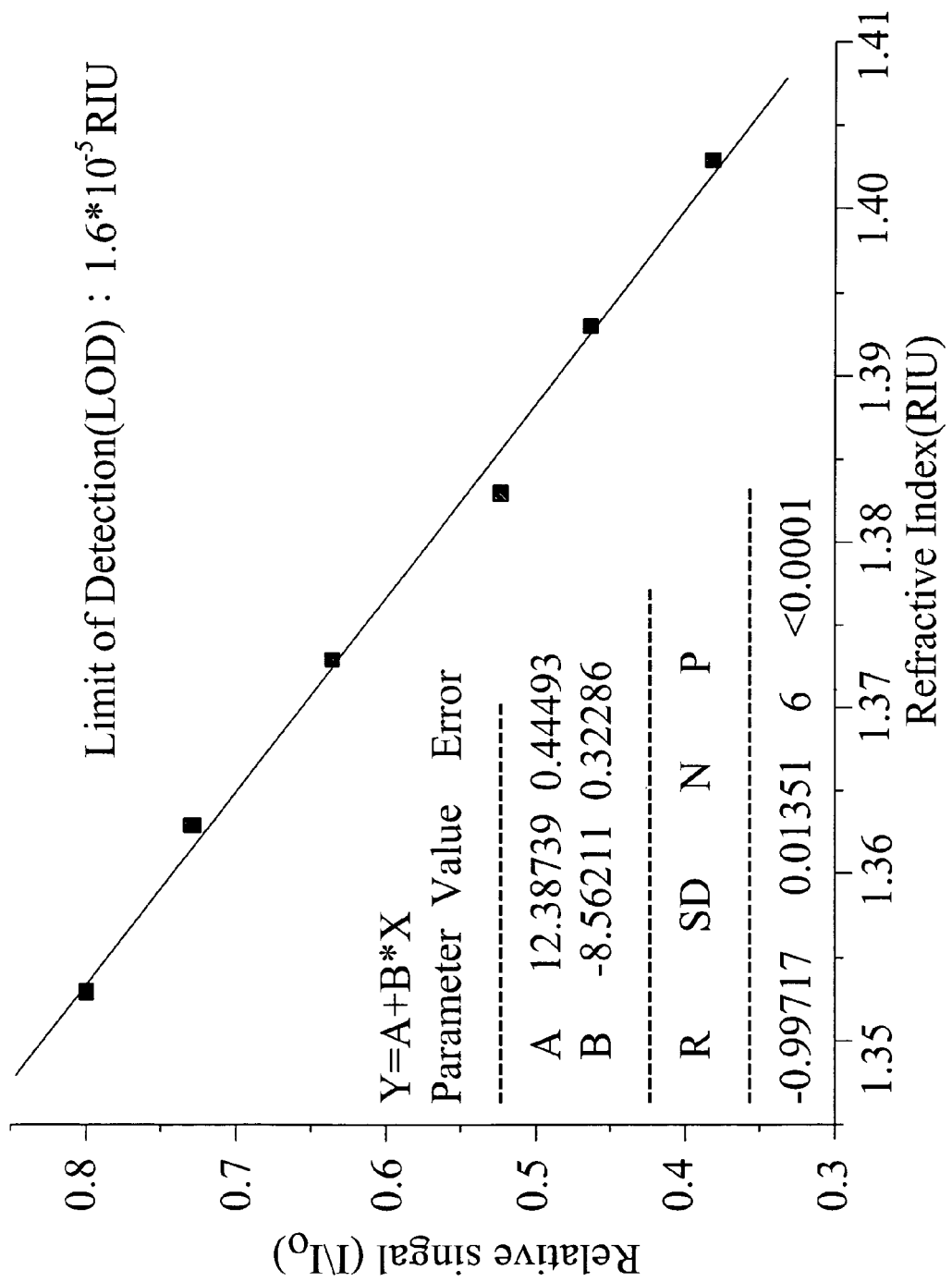
FIG. 7B is a graph of relative signal (I/Io) versus sample refractive index obtained by a second preferred embodiment of the present invention.

Seven optical fibers are used for collecting light signals of two LEDs, and then the light is coupled to different locations of the wall at the open end of the glass tube to improve the overall effect of the LPR phenomenon of the gold nanoparticles on the emergent light signal, in hope of improving the testing sensitivity. In FIG. 7A, aqueous solutions with different refractive indexes (1.333 RIU~1.403 RIU) are contained in the glass tube, the emergent light intensity of the waveguide sensor will decrease with the increase of refractive index. According to the result as shown in FIG. 7A, we plot the graph of relative intensity of emergent light (I/Io) versus refractive index. In FIG. 7B, we obtain a substantial linear regression line (R=0.9972) and derive its sensor resolution to be equal to $1.6 \times 10^{-5}$ RIU, and the experimental results show that the structure with a plurality of optical fiber as light coupling components definitely has a better sensing capability.

With reference to FIG. 8, we used three optical fibers to collect the emitted light from three LEDs in the experiment, and coupled the light to different locations of a wall of the glass tube at the open end (as shown in 3B). This design increases the effect of the LPR phenomenon of the gold nanoparticles on the emergent light intensity, and thus theoretically it may improve the sensing capability of the system.

Figure 8B:
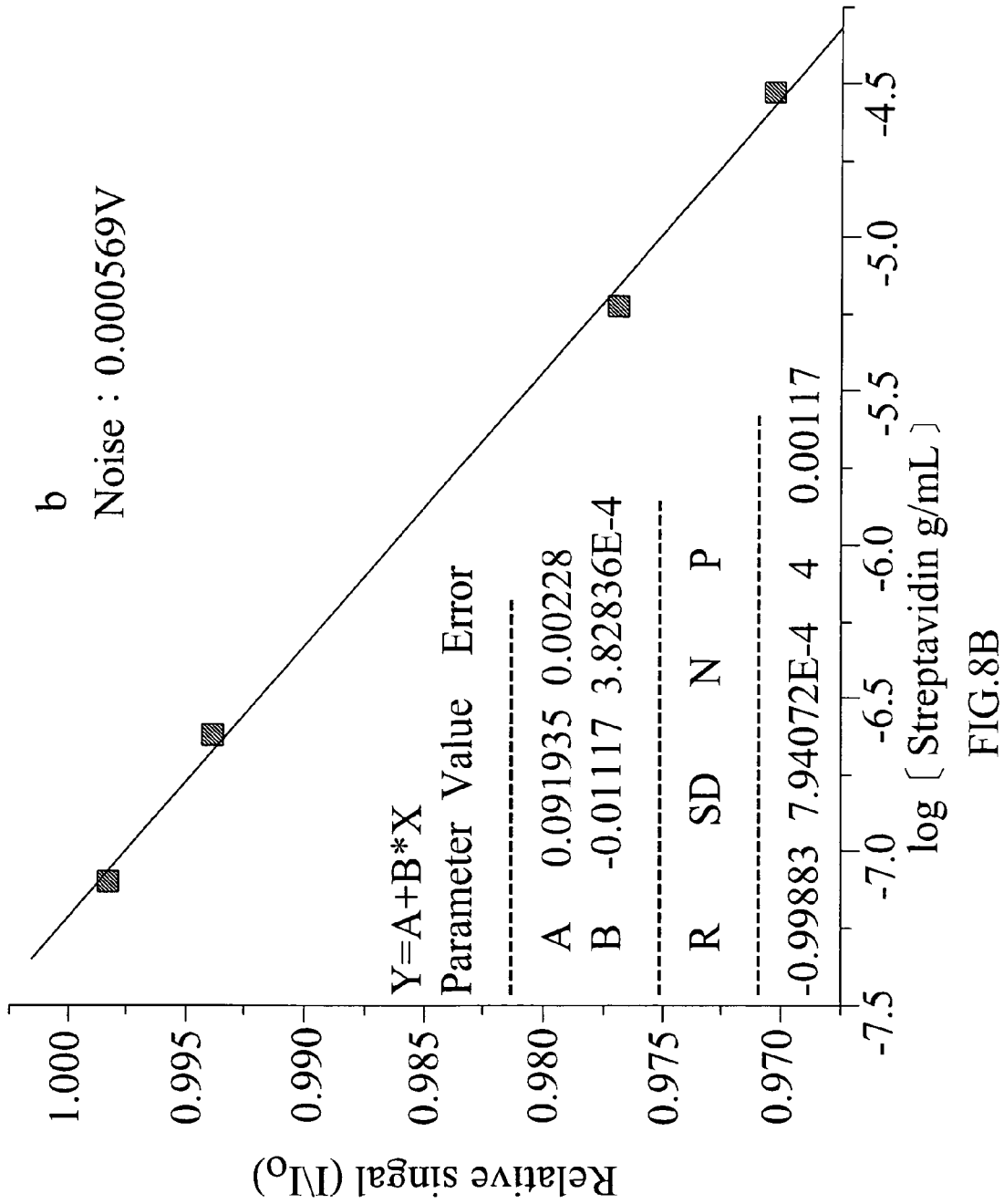
FIG. 8B is a graph of relative signal (I/Io) versus logarithm concentration of streptavidin obtained by using a plurality of point light sources in accordance with a third preferred embodiment of the present invention.

FIG. 8A shows a graph of relative intensity of emergent light (I/Io) versus logarithm concentration of streptavidin for a result of using a plurality of point light sources to obtain steady-state signal with each sample at equilibrium in accordance with a third preferred embodiment of the present invention, the first four sample signals with lower concentrations are in the range of noises, and the next four samples with higher concentrations are outside the range of noises, where we find a linear relation (R=0.9988) as shown in FIG. 8B. In addition, the noise of the system is equal to $5.7 \times 10^{-4}$V, so that we estimate the detection limit to be equal to $8.56 \times 10^{-8}$ g/mL (or $1.42 \times 10^{-9}$M).

The result shows that when a system with a plurality of LEDs is used, more gold nanoparticles are excited, and the larger effect of the LPR phenomenon on the emergent light, and thus such system may improve the detection limit of the sensing system with a plurality of LED by approximately ten times for a single LED system.

Figure 9:
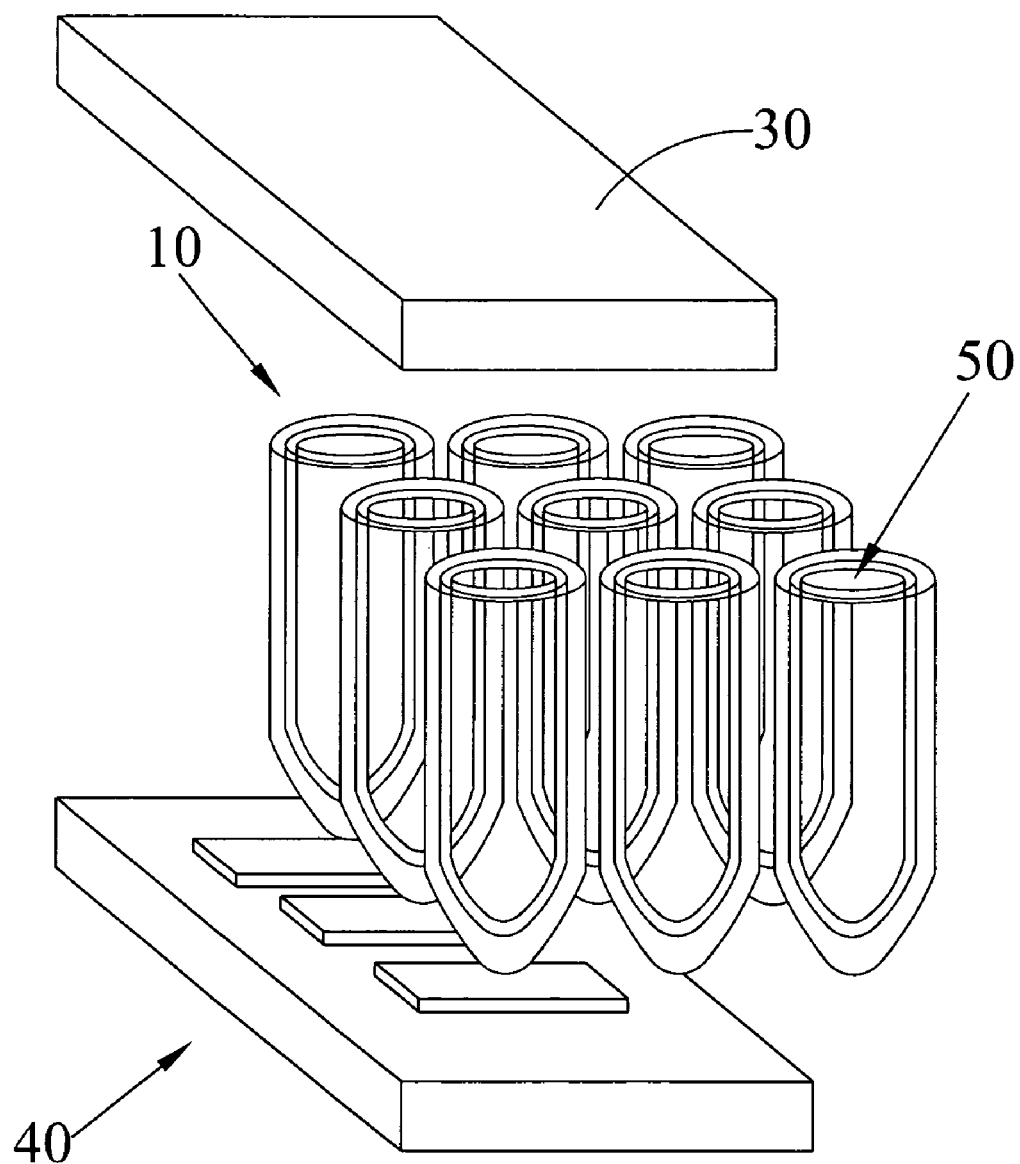
FIG. 9 is a schematic view of detecting a plurality of desired analytes in testing samples by using an array of light sources.

With reference to FIG. 9 for a schematic view of using a plurality of point light sources in an array format for detecting a plurality of desired testing samples in accordance with a third preferred embodiment of the present invention, the light source 30 may be an array of light sources, and the plurality of waveguide components 10 are arranged in an array with respect to the plurality of photon detectors 40, and the plurality of waveguide components 10 carry the plurality of desired testing samples 50, while measuring the data of a plurality of desired testing samples to achieve a testing with a high throughput. In addition, each tubular sensing unit may be designed according to actual requirements for detecting a combination of different desired testing samples.

In each of the foregoing embodiments, the waveguide component may be made of a light transmitting material, and the noble metal nanoparticle layer is composed of a plurality of gold nanoparticles, silver nanoparticles or platinum nanoparticles. In addition, different types of recognition units may be used for modifying the noble metal nanoparticle surface, and the recognition unit may be a chemical recognition molecule, an antibody, an antigen, a lectin, a hormone receptor, a nucleic acid or a saccharide, and the recognition unit is provided for detecting a metal ion, an antibody, an antigen, a cytokine, a hormone, a growth factor, a neuropeptide, a hemoglobin, a plasma protein, an amino acid, a vitamin, a nucleic acid, a carbohydrate, a glycoprotein, a fatty acid, a phosphatidic acid, a sterol, an antibiotic, a cell, a toxin, a virus or a bacterium. For instance, if a molecule with a metal ion chelating capability is used for modifying a noble metal nanoparticle surface, the specific quantity of a metal ion in a sample may be measured. For the modification with an antibody, a sensor may be used for detecting a specific antigen. On the other hand, a specific antigen may be used for the modification to detect a specific antibody. The modification of the noble metal nanoparticle surface with ribonucleic acid (RNA) or deoxyribonucleic acid (DNA) may be used for detecting genetic sample with a specific sequence, and other modifications such as a modification with a saccharide may be used for detecting bacteria.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiment(s) of the present invention.

What is claimed is:

1. A localized plasmon resonance sensing apparatus, comprising:
    a tubular waveguide component, having a tubular internal wall and a sealed bottom, the tubular waveguide component allowing a plurality of total internal reflections of an incident light, which is consisting of a single frequency light or a narrowband light, such that the incident light enters into and exits from opposite sides of the tubular waveguide component; and
    a noble metal nanoparticle layer, composed of a plurality of noble metal nanoparticles each consisting of a noble metal and disposed on a surface of the tubular internal wall;
    wherein when a desired testing sample is disposed inside the tubular waveguide component, the noble metal nanoparticles contact with the desired testing sample and results in a signal change of light attenuation of said incident light by a localized plasmon resonance effect, wherein the plurality of total internal reflections of the incident light by the tubular waveguide component accumulates the signal change of light attenuation to thereby improve sensitivity of the localized plasmon resonance sensing apparatus.

2. The localized plasmon resonance sensing apparatus of claim 1, wherein the noble metal nanoparticles are nanorods in shape.

3. The localized plasmon resonance sensing apparatus of claim 1, wherein the noble metal nanoparticles are nanospheres or nanoshells in shape.

4. The localized plasmon resonance sensing apparatus of claim 1, wherein each of the noble metal nanoparticles is modified with a recognition unit to be applied for testing different samples.

5. The localized plasmon resonance sensing apparatus of claim 4, wherein the recognition unit is a chemical recognition molecule, an antibody, an antigen, a lectin, a hormone receptor, a nucleic acid or a saccharide.

6. The localized plasmon resonance sensing apparatus of claim 5, wherein the recognition unit is used for sensing a metal ion, an antibody, an antigen, a cytokine, a hormone, a growth factor, a neuropeptide, a hemoglobin, a plasma protein, an amino acid, a vitamin, a nucleic acid, a carbohydrate, a glycoprotein, a fatty acid, a phosphatidic acid, a sterol, an antibiotic, a cell, a toxin, a virus or a bacterium.

7. The localized plasmon resonance sensing apparatus of claim 1, wherein the noble metal is gold, silver or platinum.

8. A localized plasmon resonance sensing system, comprising:
    at least one light source, for providing at least one incident light consisting of a single frequency light or a narrowband light;
    at least one tubular waveguide component, having a sealed bottom and a tubular internal wall, the tubular waveguide component allowing a plurality of total internal reflections of the incident light;
    a noble metal nanoparticle layer, composed of a plurality of noble metal nanoparticles each consisting of a noble metal and disposed on the tubular internal wall for contacting a desired testing sample; and
    at least one photon detector, for detecting at least one emergent light exiting the tubular waveguide component after an interaction of the noble metal nanoparticles with the desired testing sample, wherein the light source and the photon detector are located on two opposite sides of the tubular waveguide component;
    wherein when the desire testing sample is disposed inside the tubular waveguide component, the noble metal nanoparticles contact with the desired testing sample and results in a signal change of light attenuation by a localized plasmon resonance effect, wherein the plurality of total internal reflections of the incident light by the tubular waveguide component accumulates the signal change of light attenuation to thereby improve sensitivity of the localized plasmon resonance sensing apparatus.

9. The localized plasmon resonance sensing system of claim 8, wherein at least one light source is an independent light or a moving light source.

10. The localized plasmon resonance sensing system of claim 8, wherein the noble metal nanoparticles are nanorods in shape.

11. The localized plasmon resonance sensing system of claim 8, wherein the plurality of tubular waveguide components are arranged in an array corresponding to the plurality of photon detectors.

12. The localized plasmon resonance sensing system of claim 8, further comprising at least one first optical fiber, for coupling the incident light from the light source and transmitting the incident light to be incident into the tubular waveguide component.

13. The localized plasmon resonance sensing system of claim 8, further comprising a lens and a second optical fiber, and the lens being provided for collecting the emergent light and transmitting the emergent light to the photon detector through the second optical fiber.

14. The localized plasmon resonance sensing system of claim 8, further comprising a function generator for driving a light source so that an incident light is modulated.

15. The localized plasmon resonance sensing system of claim 8, further comprising a lock-in amplifier for reducing a system noise.

16. The localized plasmon resonance sensing system of claim 8, wherein each of the noble metal nanoparticles is modified with a recognition unit to be applied for testing different samples.

17. The localized plasmon resonance sensing system of claim 16, wherein the recognition unit is a chemical recognition molecule, an antibody, an antigen, a lectin, a hormone receptor, a nucleic acid or a saccharide.

18. The localized plasmon resonance sensing system of claim 17, wherein the recognition unit is used for sensing a metal ion, an antibody, an antigen, a cytokine, a hormone, a growth factor, a neuropeptide, a hemoglobin, a plasma protein, an amino acid, a vitamin, a nucleic acid, a carbohydrate, a glycoprotein, a fatty acid, a phosphatidic acid, a sterol, an antibiotic, a cell, a toxin, a virus or a bacterium.

19. The localized plasmon resonance sensing system of claim 8, wherein the noble metal nanoparticles are nanospheres or nanoshells in shape.

20. The localized plasmon resonance sensing system of claim 8, wherein the noble metal is gold, silver or platinum.

* * * * *